(12) United States Patent
O'Rourke et al.

(10) Patent No.: US 7,981,103 B2
(45) Date of Patent: Jul. 19, 2011

(54) METHOD OF TREATING A STIFFENED BLOOD VESSEL

(75) Inventors: Michael O'Rourke, Hunters Hill New South Wales (AU); William Walsh, Maroubra New South Wales (AU); Jim Iliopoulos, Bexley North New South Wales (AU); Alberto Pompeo Avolio, North Bondi New South Wales (AU); Ronald Mark Gillies, Enmore (AU); Peter Walsh, Everton Park Queensland (AU)

(73) Assignee: Aortic Wrap Pty Ltd. (AU)

( * ) Notice: Subject to any disclaimer, the term of this patent is extended or adjusted under 35 U.S.C. 154(b) by 825 days.

(21) Appl. No.: 10/540,306

(22) PCT Filed: Dec. 19, 2003

(86) PCT No.: PCT/AU03/01699
§ 371 (c)(1),
(2), (4) Date: Jun. 20, 2005

(87) PCT Pub. No.: WO2004/056274
PCT Pub. Date: Jul. 8, 2004

(65) Prior Publication Data
US 2006/0052866 A1  Mar. 9, 2006

(30) Foreign Application Priority Data
Dec. 19, 2002  (AU) ................................ 2002953440

(51) Int. Cl.
*A61M 31/00* (2006.01)
(52) U.S. Cl. ........................................................ 604/507
(58) Field of Classification Search ......... 623/1.11–1.54
See application file for complete search history.

(56) References Cited

U.S. PATENT DOCUMENTS

| | | | | |
|---|---|---|---|---|
| 3,726,279 | A * | 4/1973 | Barefoot et al. | 606/151 |
| 4,202,349 | A * | 5/1980 | Jones | 600/502 |
| 4,834,755 | A * | 5/1989 | Silvestrini et al. | 623/13.19 |
| 5,057,118 | A * | 10/1991 | Picha | 606/158 |
| 5,304,200 | A * | 4/1994 | Spaulding | 623/1.16 |
| 5,314,472 | A * | 5/1994 | Fontaine | 623/1.22 |
| 5,387,235 | A * | 2/1995 | Chuter | 623/1.11 |
| 6,726,923 | B2 * | 4/2004 | Iyer et al. | 424/443 |
| 6,984,201 | B2 * | 1/2006 | Khaghani et al. | 600/17 |
| 2001/0007082 | A1 * | 7/2001 | Dusbabek et al. | 623/1.11 |
| 2002/0116016 | A1 * | 8/2002 | Barath | 606/153 |

(Continued)

FOREIGN PATENT DOCUMENTS

SU  566567  7/1977

(Continued)

OTHER PUBLICATIONS

International Search Report for PCT/AU2003/001699 dated Mar. 4, 2004.

(Continued)

*Primary Examiner* — David Isabella
*Assistant Examiner* — Ann Schillinger
(74) *Attorney, Agent, or Firm* — Kilpatrick Townsend & Stockton LLP

(57) ABSTRACT

A method of treating a stiffened blood vessel (2) is disclosed. The method comprises at least substantially encasing a portion of the blood vessel (2) with an elastic membrane (6) formed of biocompatible material such the membrane (6) engages the blood vessel (2) to thereby reduce the diameter of the blood vessel (2).

29 Claims, 11 Drawing Sheets

U.S. PATENT DOCUMENTS

| | | | | |
|---|---|---|---|---|
| 2002/0151959 A1* | 10/2002 | Von Oepen | ................... | 623/1.15 |
| 2003/0065303 A1* | 4/2003 | Wellman et al. | .............. | 604/500 |
| 2004/0010303 A1* | 1/2004 | Bolea et al. | ................... | 607/118 |
| 2004/0147803 A1* | 7/2004 | Hegde et al. | .................... | 600/16 |

FOREIGN PATENT DOCUMENTS

| | | |
|---|---|---|
| SU | 566567 A | 8/1977 |
| WO | WO 96/73371 A1 | 3/1996 |
| WO | WO 01/21106 A1 | 3/2001 |
| WO | WO 03/011190 A2 | 2/2003 |

OTHER PUBLICATIONS

Supplementary Partial European Search Report of European Application No. 03767299, dated Feb. 27, 2009, 3 pages total.

* cited by examiner

METHOD OF TREATING A STIFFENED BLOOD VESSEL

TECHNICAL FIELD

The present invention relates to the treatment of a stiffened blood vessel, and in particular relates to, but is not limited to, a method of treating a stiffened and dilatated aorta to reduce cardiac load and increase coronary perfusion.

BACKGROUND OF THE INVENTION

The left ventricle of the heart pumps cyclically to deliver oxygenated blood to the body via the aorta. The cyclic pumping of the left ventricle of the heart includes a systole stage and a diastole stage, depicted in FIGS. 1 and 2 respectively.

During the systole stage, the left ventricle 1 contracts, pumping blood to the aorta 2 through the aortic valve 3. Contraction of the left ventricle 1 increases the pressure in the aorta 2, causing the aorta 2 to expand, as depicted in FIG. 1. The expansion absorbs some of the shock loading associated with ejection of blood from the left ventricle. At various points 4 along the aorta, the aorta wall may be subject to anatomical constraints restricting the ability of the aorta to expand. The systolic blood pressure is the maximum blood pressure in the aorta during the systole stage.

During the diastole stage, the left ventricle 1 relaxes and the aortic valve 3 closes to stop back flow of blood into the left ventricle 1. The left atrium 5 contracts to fill the left ventricle 1 with further blood in preparation for the next systole stage. During the diastole stage, the blood pressure within the aorta 2 reduces to what is termed the diastolic blood pressure. The reduced pressure at this stage causes the wall of the aorta 2 to recoil (contract), restoring it back to its original diameter. The blood is accordingly pumped through the aorta and into the arteries in a pulsating manner.

The ability of the aorta 2 to expand and recoil during the systole and diastole stages is dependent upon the elasticity of the aorta wall which is a result of the elastin fibres present in the aorta wall.

Systolic blood pressure progressively increases with ageing that begins in childhood until the eighth or ninth decade, whereas diastolic blood pressure tends to remain constant in the fifth or sixth decade but decreases thereafter. Consequently, the pulse pressure, being the pressure differential between the systolic and diastolic blood pressure, increases with ageing. This form of hypertension is termed isolated systolic hypertension and increases in frequency with increasing age.

Various studies have shown that elevated systolic pressure is associated with a greater risk of heart failure, stroke, and acute myocardial infarction, and that treatment of elevated systolic pressure can delay or prevent such adverse events even when diastolic pressure is normal or low.

A number of studies have also shown that, in patients over 50, there is a stronger association between adverse cardiovascular (particularly coronary) events and pulse pressure, than systolic or diastolic pressure in isolation. Accordingly, for any given systolic pressure, the diastolic pressure is inversely related to the risk of adverse cardiovascular events, possibly due to reduction in coronary perfusion with decreased diastolic pressure.

Heart failure is reported to effect 2 to 5 percent of people in Western societies aged over 65, and 10 percent of those aged over 75. It is also reported to be the leading cause of hospital admission and readmission in Americans older than 65.

The increase in systolic blood pressure with age is largely a result of stiffening of the aorta and large elastic arteries. Dilatation of the aorta/arteries is typically associated with this stiffening. The stiffening and dilatation is a result of the repetitive cyclic stress applied to the aorta wall during expansion and subsequent relaxation of the aorta. The cyclic stresses applied to the aorta wall result in fatigue, fracture and fragmentation of the elastin fibres which provide the aorta wall with its elasticity. The mechanical properties of the aorta wall gradually become dominated by inelastic collagen. The breakdown of the elastin fibres results in the aorta becoming inelastic and stiff, thereby losing its capability to restore to its original diameter after expansion during the systole stage. The aorta accordingly remains permanently dilatated.

A young, healthy ascending aorta typically has an external diameter of the order of 25 mm when subjected to normal diastolic pressure of 70 mmHg (9.3 kPa), and a wall thickness of the order of 1 mm. The diameter and wall thickness decrease from the proximal portions of the aorta to the more distal portions. Dilatation of the aorta associated with aortic stiffening may result in an increase in the external diameter of the ascending aorta at diastolic pressure to as large as 40 mm or more.

Measurement of the stiffness of the aorta has been the subject of various studies, measuring various different stiffness related properties. The measurement of pure tensile stiffness of a section of aorta, providing a Young's modulus, is not readily obtained given the non-homogeneous nature of the aorta. A common, and more meaningful, stiffness measurement is the pressure-strain elastic modulus ($E_p$):

$$E_p = (dP/dD) \times D$$

where D=aortic diameter;
dD=change in aortic diameter;
dP=change in aortic pressure.

The aortic stiffness is non-linear, increasing with increasing pressure, partly due to the biochemical, structural and geometric makeup of the extracellular matrix of the aorta wall, and hence the aortic stiffness at a specified pressure is measured as the tangent to the pressure/diameter curve. Stiffness can most meaningfully be measured as the average stiffness over the range of pressures experienced during physiological flow as follows:

$$E_p = (dP/dD) \times D$$

where D=diastolic aortic diameter;
dD=pulsatile change in aortic diameter (systolic diameter minus diastolic diameter)
dP=pulse pressure (systolic pressure minus diastolic pressure)

This stiffness varies greatly from subject to subject, and increases from the proximal portions of the aorta to the more distal portions. A typical young, healthy ascending aorta will have a stiffness ($E_p$) of about $0.41 \times 10^6$ dyn/cm$^2$ (41 kPa). A stiffened ascending aorta may have an increased stiffness of up to $16 \times 10^6$ dyn/cm$^2$ (1600 kPa) or more.

Aortic stiffening alters the left ventricular systolic pressure in two ways. First, there is a greater rise in pressure at the time of peak aortic flow in the systole stage as a result of failure of the aorta to expand as blood is pumped from the left ventricle. Secondly, aortic stiffening increases the pulse wave velocity in the large blood vessels. This causes pressure waves reflected from peripheral sites to return to the aorta earlier than usual, boosting pressure in the late systole stage. This early return of the reflected wave to the ascending aorta during the ventricular ejection of systole is detrimental since systolic pressure and left ventricular afterload is increased.

The early return of the reflected wave also reduces diastolic pressure and the capacity for myocardial perfusion. Each of these factors results in an increase in cardiac load of the left ventricle.

The most effective means of treating, or preventing, heart failure is to reduce cardiac load either pharmacologically or mechanically. Mechanical reduction of cardiac load using intra-aortic balloon counter pulsation and ventricular assist devices have proven effective. However, intra-aortic balloon counter pulsation can only be used as a temporary treatment. Ventricular assist devices are also expensive and temporary measures.

OBJECT OF THE INVENTION

It is an object of the present invention to overcome or substantially ameliorate at least one of the above disadvantages.

SUMMARY OF THE INVENTION

In a first aspect, the present invention provides a method of treating a stiffened blood vessel, the method comprising at least substantially encasing a stiffened portion of said blood vessel with an elastic membrane formed of biocompatible material such that said membrane engages said stiffened portion of said blood vessel to thereby reduce the external diameter of said stiffened portion of said blood vessel.

Preferably the blood vessel is an artery.

More preferably the blood vessel is the aorta, particularly the ascending aorta.

The stiffened portion of said blood vessel may be a grafted synthetic portion of blood vessel. The grafted synthetic portion may be a woven polyester graft. Alternatively, the grafted synthetic portion may be a polytetrafluoroethylene or Gore-Tex® graft.

The stiffened portion of said blood vessel may be dilatated prior to treatment.

The membrane may be in the form of a sheet, said stiffened portion of said blood vessel being encased by wrapping said membrane sheet around the circumferential periphery of said stiffened portion of said blood vessel and securing opposing end portions of said membrane.

The membrane sheet may be wrapped around either the entire circumferential periphery of said stiffened portion of said blood vessel, or only about a majority of the circumferential periphery.

The opposing end portions of said membrane sheet may be secured by suturing.

Alternatively, the opposing end portions of said membrane may be secured by way of a clamp, or by welding.

In another form, the opposing end portions of said membrane may be secured by way of interlocking structures formed on, or fixed to, each of said opposing end portions.

Each opposing end portion may be provided with a marking extending generally parallel with a free end edge of said end portion, said end portions being secured along or adjacent to said markings.

The membrane sheet may be formed by slitting a cylindrical membrane.

The membrane may be in the form of a spiral, said stiffened portion of said blood vessel being encased by spirally wrapping said membrane spiral around the circumferential periphery of said stiffened portion of said blood vessel.

Typically, said membrane has a stiffness approximating that of a non-stiffened blood vessel of the type of blood vessel being treated.

The membrane may have a measurement of tensile stiffness×thickness of between 25 and 2500 N/m, or optionally more specifically between 50 and 1000 N/m.

The membrane, when formed into a cylinder having an internal diameter of 20 mm, may have an average pressure-strain elastic modulus of between $0.15 \times 10^6$ and $15 \times 10^6$ dyn/cm$^2$ at a pulsatile pressure of 120/70 mmHg (16/9 kPa), or optionally more specifically between $0.3 \times 10^6$ and $6 \times 10^6$ dyn/cm$^2$.

The external diameter of said stiffened portion of said blood vessel may be reduced by between 10% and 50% when encased with said membrane, at a pressure of 70 mmHg (9 kPa)

When the blood vessel is the ascending aorta, the external diameter of said stiffened portion of said blood vessel may be reduced to between 18 and 30 mm at a pressure of 70 mmHg.

The membrane may be formed of an elastic silicon polymer or elastic polyurethane material.

Preferably, said method is carried out thoracoscopically.

In a second aspect, the present invention provides a method of treating a blood vessel, said blood vessel having a native tissue portion and a synthetic portion grafted in line with said native tissue portion, said synthetic portion having a greater stiffness than the stiffness of said native tissue portion, said method comprising at least substantially encasing said synthetic portion with an elastic membrane formed of biocompatible material such that said membrane engages said synthetic portion to thereby reduce the diameter of said synthetic portion.

In a third aspect, the present invention provides a device for treating a stiffened blood vessel, said device comprising an elastic membrane formed of a sheet of biocompatible material having two opposing end portions, said membrane being adapted to be wrapped around the circumferential periphery of a stiffened portion of said blood vessel and said opposing end portions secured to each other to thereby reduce the external diameter of said stiffened portion of said blood vessel, wherein each said end portion is provided with a marking extending generally parallel with a free end edge of said end portion, said marking being indicative of the location at which said opposing end portions are to be secured with said membrane wrapped about said stiffened portion of said blood vessel, the distance between said end markings being selected as the circumference of a cylinder to be formed by wrapping said membrane sheet around said stiffened portion of said blood vessel.

The distance between said markings may be between 56 and 94 mm (corresponding to a cylinder diameter of between 18 and 30 mm).

In a fourth aspect, the present invention provides a device for treating a stiffened blood vessel, said device comprising an elastic membrane formed of a sheet of biocompatible material having two opposing end portions, said membrane being adapted to be wrapped around the circumferential periphery of a stiffened portion of said blood vessel, wherein said device further comprises interlocking structures formed on, or fixed to, each said opposing end portion for securing said end portions about said stiffened portion of blood vessel to thereby reduce the external diameter of said stiffened portion of said blood vessel.

In a fifth aspect, the present invention provides a device for treating a stiffened blood vessel, said device comprising an elastic membrane formed of a sheet of biocompatible material having two opposing end portions, said membrane being adapted to be wrapped around the circumferential periphery of a stiffened portion of said blood vessel and said opposing end portions secured to each other to thereby reduce the external diameter of said stiffened portion of said blood vessel, wherein a series of generally parallel markings are applied to a surface of said membrane.

Typically, each of said markings extends generally parallel to a free end edge of each of said end portions.

In a sixth aspect, the present invention provides a device for treating a stiffened blood vessel, said device comprising an elastic membrane formed of a sheet of biocompatible material having two opposing end portions, said membrane being adapted to be wrapped around the circumferential periphery of a stiffened portion of said blood vessel, wherein said membrane includes a radio-opaque marker.

The radio-opaque marker may be dispersed throughout said membrane.

Alternatively, the radio-opaque marker may be applied to a surface of said membrane.

The radio-opaque marker may comprise tantalum.

Alternatively, the radio-opaque marker may comprise barium sulphate or zirconium dioxide.

BRIEF DESCRIPTION OF THE DRAWINGS

Preferred forms of the present invention will now be described by way of example with reference to the accompanying drawings, wherein.

DETAILED DESCRIPTION OF THE PREFERRED EMBODIMENTS

Figure 1:
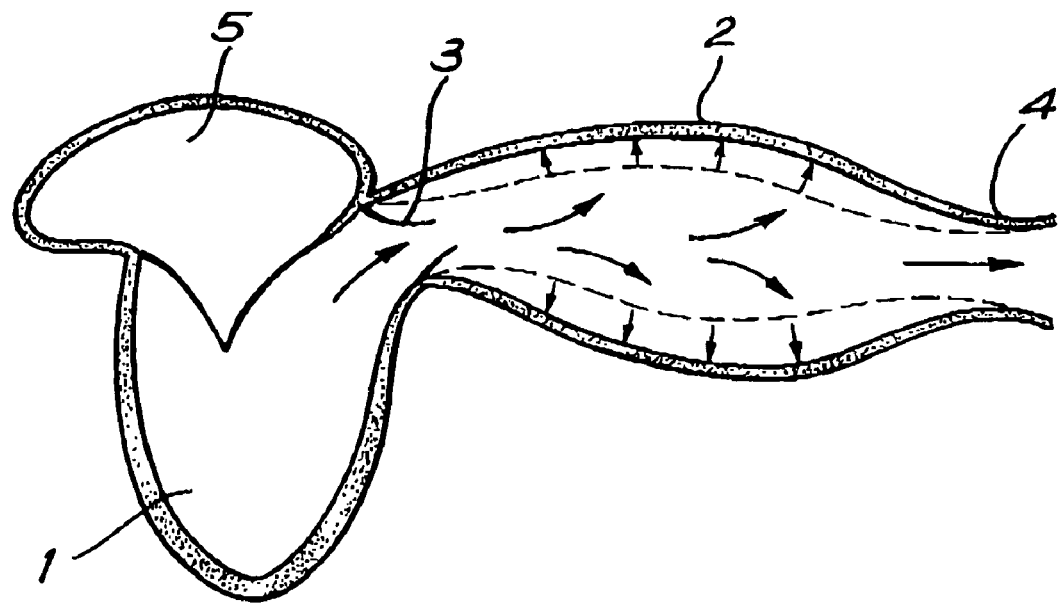
FIG. 1 is a schematic partial cross-sectional view of a heart and aorta in systole.
Figure 2:
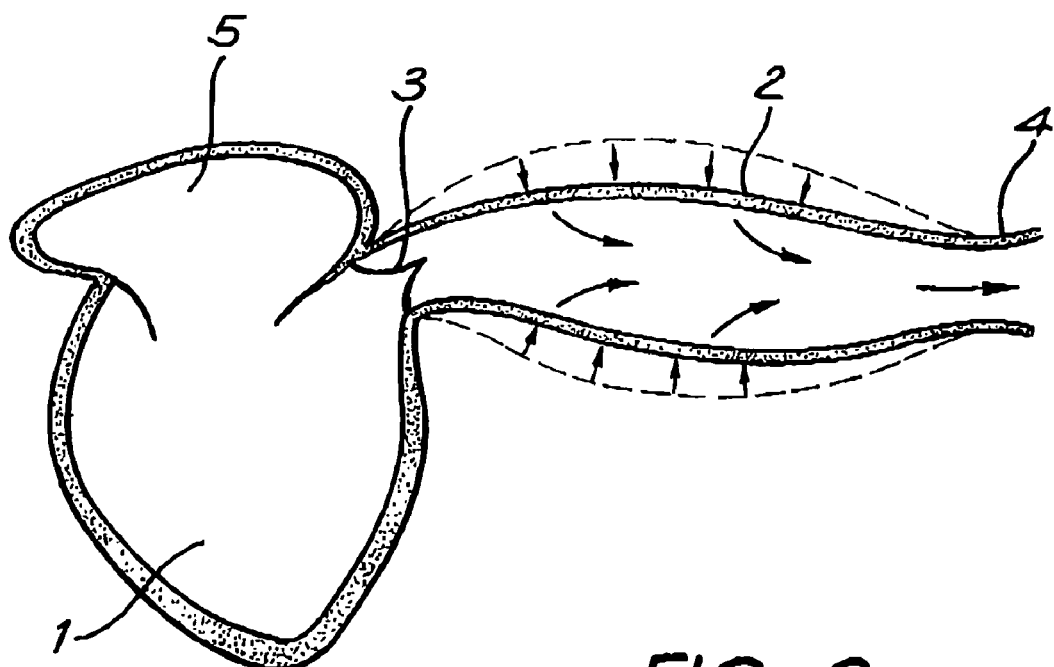
FIG. 2 is a schematic partial cross-sectional view of the heart and aorta of FIG. 1 in diastole.
Figure 3:
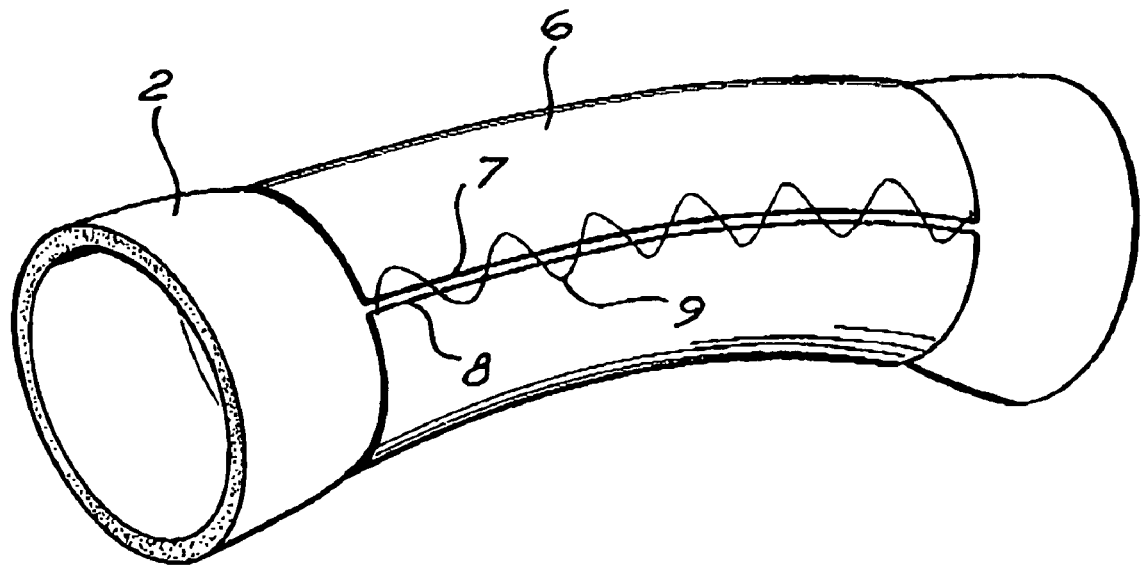
FIG. 3 is a perspective view of a portion of an aorta encased by a membrane.
Figure 4:
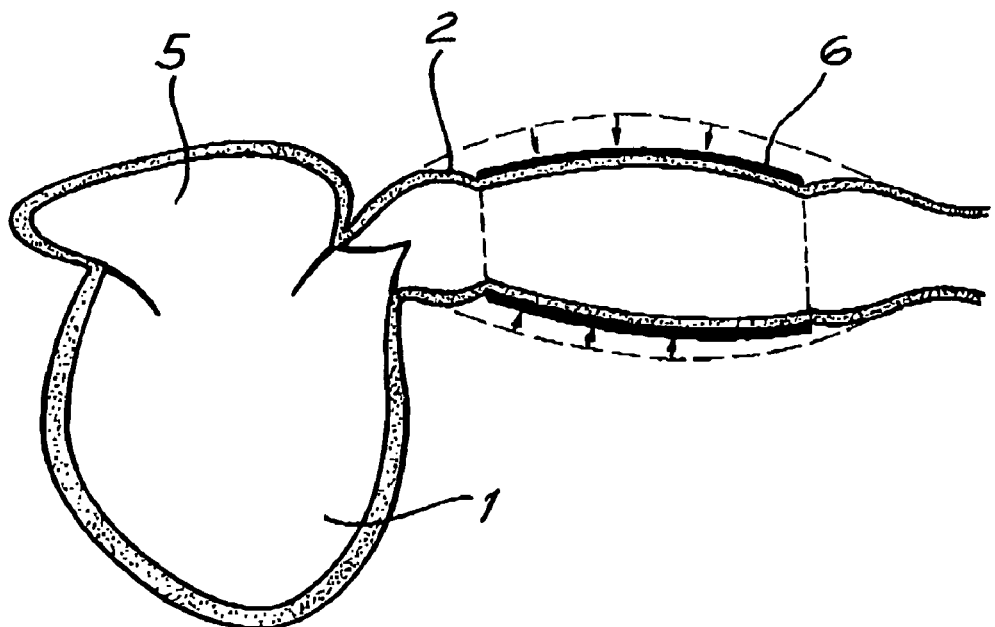
FIG. 4 is a schematic cross-sectional view of the aorta portion of FIG. 3.

Referring specifically to FIGS. 3 and 4, a stiffened and dilatated aorta 2 is treated by at least substantially encasing a portion of the aorta 2 with an elastic membrane 6. The elastic membrane 6 engages the wall of the aorta 2, contracting the dilatated aorta to reduce its diameter back towards that of the healthy aorta in the diastole stage (as per that depicted in FIG. 2). The membrane 6 will accordingly contract the aorta 2 in the diastole stage and most internal blood pressure loads during diastole acting on the aorta wall will be largely carried by the elastic membrane 6. As blood pressure increases during the systole stage, the increasing pressure acting on the membrane 6 will stretch the membrane 6, allowing the aorta 2 to expand back towards its dilatated state in the usual manner. If the elastic membrane 6 has a stiffness and diameter approximating that of a non-stiffened aorta, the elastic membrane 6 will take a substantial portion of the load applied by the blood pressure during systole, as the aorta 2 will only start to take up any appreciable load once expanded beyond its now naturally permanently enlarged state.

With a substantial portion of the load placed on the aorta during the diastole and systole stages being carried by the elastic membrane 6, the effective stiffness of the encased portion of aorta 2 will be similar to that of the elastic membrane 6. Accordingly, if the stiffness of the elastic membrane 6 approximates that of a non-stiffened aorta, the aorta 2 will expand and restore in much the same manner as a healthy aorta.

Reducing the effective stiffness of the aorta 2 in this manner, providing for elastic expansion of the aorta 2 during the systole stage, will reduce ascending aortic and left ventricular pressure during systole. Similarly, with the encased aorta 2 being restored to its reduced diameter during diastole, the diastolic pressure will increase in the same general manner as for a healthy aorta.

Decreasing aortic and left ventricular pressure during systole will aid left ventricular ejection and reduce left ventricular load, especially in the presence of cardiac failure, and decrease myocardial oxygen demand. The increase in aortic diastolic pressure resulting from a more normal recoil of the aorta during diastole will improve myocardial blood flow and oxygen supply. The reduction in pulse pressure resulting from a decrease of systolic pressure and increase in diastolic pressure will reduce pulsatile external work and thus increase the efficiency of blood circulation. An effective treatment to reduce cardiac load is thus provided using a simple, passive device.

Figure 5:
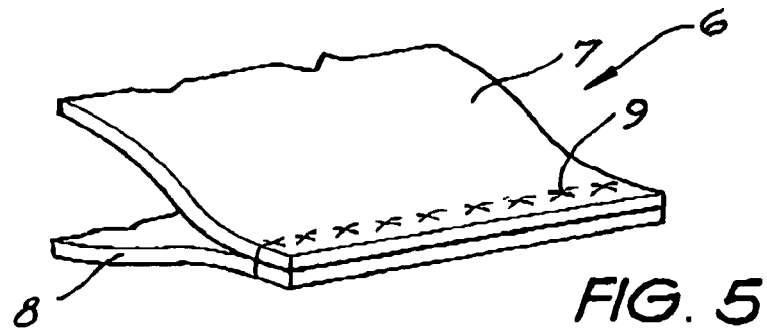
FIG. 5 is a perspective view of the end portions of a membrane secured by sutures.

The membrane 6 depicted in FIG. 3 is in the form of a membrane sheet which encases the aorta portion 2 by wrapping the membrane sheet 6 around the circumferential periphery of the aorta and securing opposing end portions 7, 8 of the membrane sheet 6. The membrane end portions 7, 8 may be secured by a suture 9 in a manner indicated in FIG. 3. Alternatively, and more practically, the membrane end portion 7, 8 may be secured by a suture 9 in the manner depicted in FIG. 5 with the inner faces of the end portions 7, 8 abutting.

Figure 6:
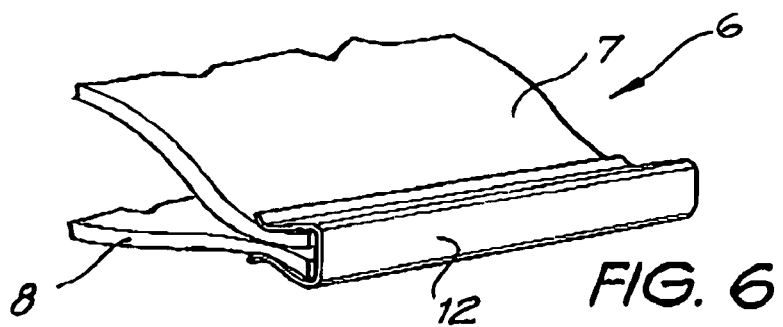
FIG. 6 is a perspective view of the end portions of a membrane secured by a clamp.

Rather than suturing, the membrane end portions 7, 8 may be secured by way of a clamp 12 as depicted in FIG. 6. The clamp 12 is a spring-type clamp formed of a biocompatible material, typically stainless steel. As depicted in FIG. 6, the width of the clamp 12 is approximately equal to that of the membrane 6.

Figure 7:
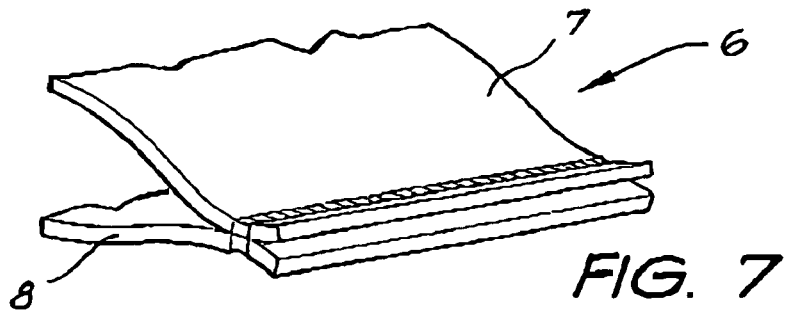
FIG. 7 is a perspective view of the end portions of a membrane secured by welding.

An alternative method of securing the membrane end portions 7, 8, depicted in FIG. 7, involves welding of the end portions, typically utilising an ultrasonic frequency dependent upon the membrane material, to cause the end portions 7, 8 to fuse together.

Figure 8:
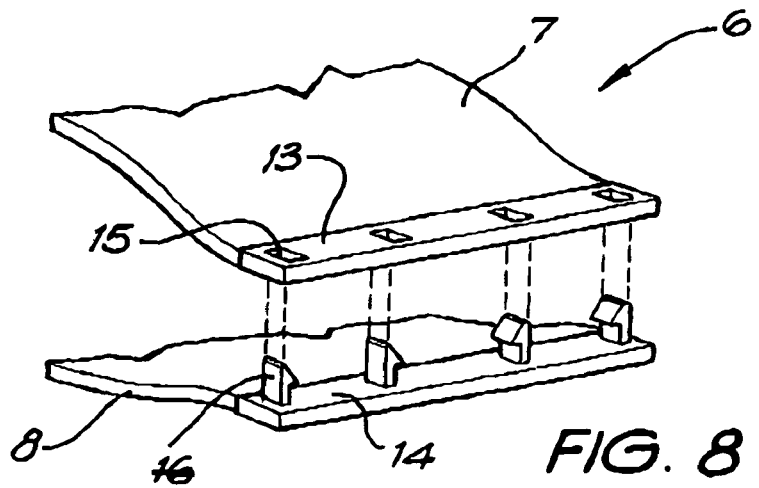
FIG. 8 is a perspective view of the end portions of a membrane secured by interlocking structures.

As a further alternative, the membrane end portions 7, 8 may be provided with interlocking structures 13, 14, as depicted in FIG. 8. Here the first interlocking structure 13 is a first strip of biocompatible plastics material fixed to the free end edge of the end portion 7, with apertures 15 extending through and being spaced along the first strip 13. The second structure is a second strip of biocompatible plastics material fixed to the free end edge of the end portion 8, with barbs 16 upstanding therefrom and spaced therealong. When the membrane 6 is wrapped around the aorta portion 2, the barbs 16 are aligned with the corresponding apertures 15. Pressing the strips 13, 14 together passes the barb 16 through the apertures 15 to form a snap-type connection. Rather than being fixed to the membrane 6, the interlocking structures 13, 14 may be integrally formed with the membrane 6.

Figure 9A:
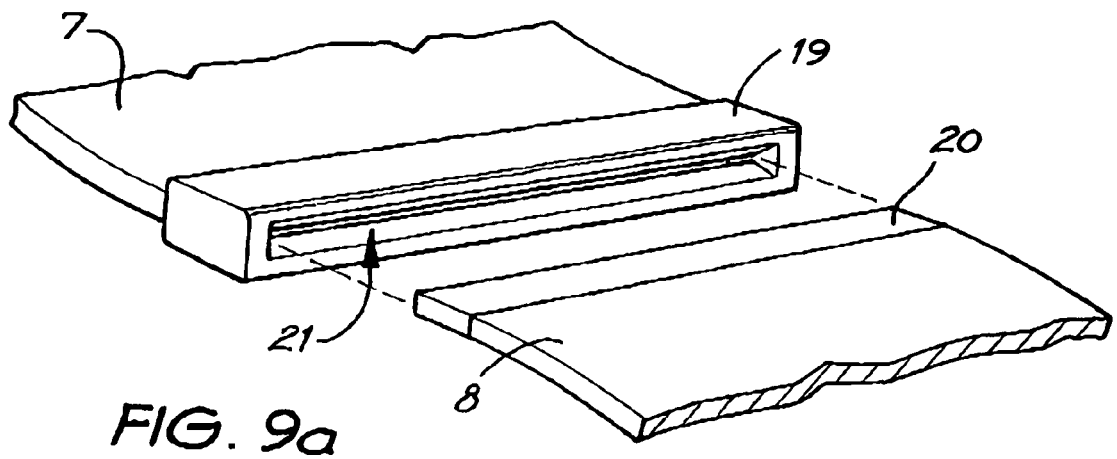
FIG. 9a is a perspective view of the end portions of a membrane having alternate interlocking structures.
Figure 9B:
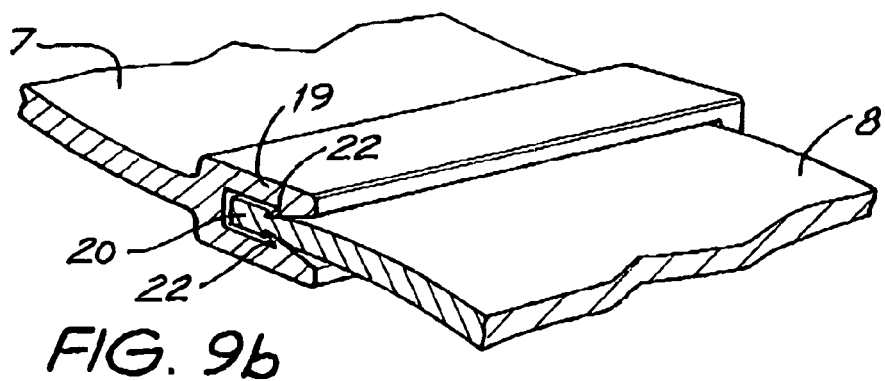
FIG. 9b is a perspective view of the membrane end portions of FIG. 9a secured by the alternate interlocking structures.
Figure 9C:
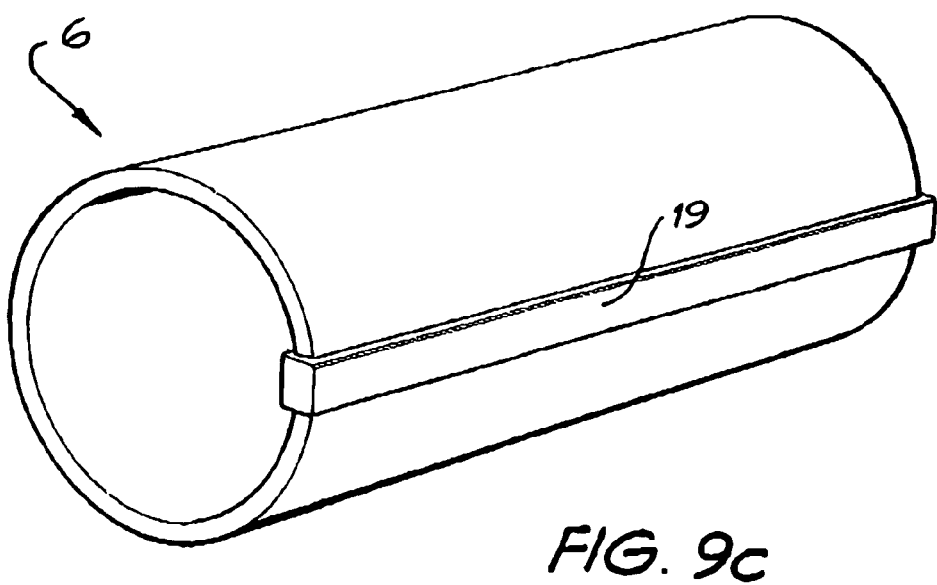
FIG. 9c is a perspective view of the membrane of FIG. 9a with end portions secured by the alternate interlocking structures.

FIGS. 9a to 9c depict a membrane 6 having membrane end portions 7, 8 provided with alternate interlocking structures 19, 20. The first structure 19 is fixed to end portion 7 and is in the form of a slotted housing 19 extending along the free end edge of the end portion 7. The housing 19 has a slot 21 extending along the length of the end portion 7. The opposing internal faces of the slot 21 are provided with elongate barbs 22. The structure 19 is formed of a resilient biocompatible material, typically a plastics material. The second structure 20, fixed to end portion 8, is in the form of a strip 20 of resilient biocompatible material, typically a plastics material. The strip 20 is sized to be received in the slot, resiliently deforming the barbs 22. Once the strip 20 passes beyond the barbs 22, the barbs "snap" back, pressing into the soft elastic membrane 6, so as to lock the strip 20 within the housing 19, thereby securing the end portions 7, 8.

Figure 10:
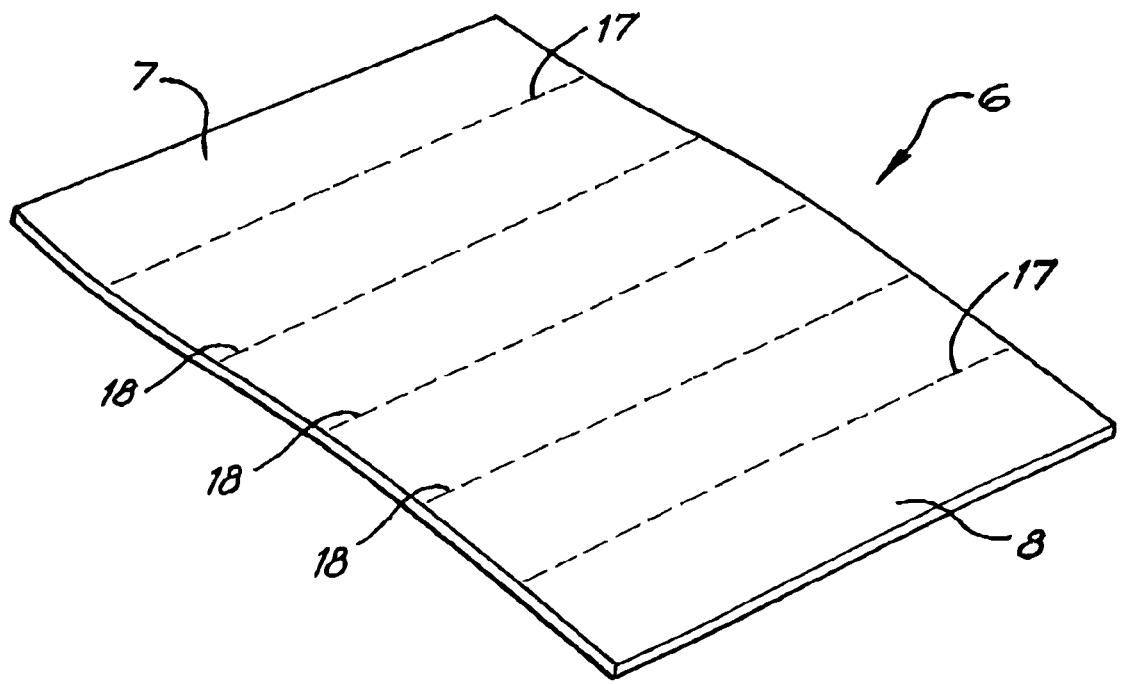
FIG. 10 is a perspective view of a membrane having markings on the end portions.

Referring to FIG. 10, to assist in ensuring a membrane 6 is wrapped about the aorta portion 2 to restrict the aorta portion to a desired diameter, markings 17 may be applied to each end portion 7, 8 generally parallel to the free edge of the end portions 7, 8. The distance between the markings 17 is selected as the circumference corresponding to the desired diameter to which the aorta portion 2 is to be restricted. For example, if the aorta portion is to be restricted to an external diameter of 20 mm, then the markings 17 are applied to the membrane 6 approximately 63 mm (pi×20 mm) apart. These markings are thus indicative of the location on the end portions 7, 8 at which the end portions 7, 8 are to be secured. In particular, if the end portions are to be secured by suturing as per the arrangement of FIG. 5, these markings indicate the line along which, or adjacent to, the suturing is to be applied. The markings 17 may be in the form of sutures extending along the end portions 7, 8 or might alternatively be printed markings applied to the membrane end portions 7, 8.

Further markings 18 may be applied to the surface of the membrane 6, again in the form of sutures or printed markings, to provide the surgeon with a visual indication of the extent of expansion and recoil of the encased aorta after having secured the membrane 6 in place but prior to closing the patient or during a subsequent visual inspection. The markings 18 may be applied as a series of parallel lines running parallel to the end portions 7, 8, such that an increase in the distance between the markings 18 will indicate expansion of the aorta 6.

The membrane may also include a radio-opaque marker. Such a radio-opaque marker may be applied to the surface of the membrane 6, optionally in the form of the markings 18, or may be dispersed throughout the membrane 6. The radio-opaque marker may take the form of any known radio-opaque marker used in surgical applications, including tantalum beads, barium sulphate or zirconium dioxide. Barium sulphate and zirconium dioxide will be particularly suitable for use dispersed throughout the membrane, being introduced in powder form with the other raw materials forming the membrane material. The use of a radio-opaque marker enables the placement and integrity of the membrane 6 to be monitored by any of various radiography techniques. Further, the use of dynamic thorascopy, real time ultrasound, angiography and magnetic resonance (MR) angiography will enable the dynamic performance of the membrane to be monitored in a non-invasive manner.

Figure 11:
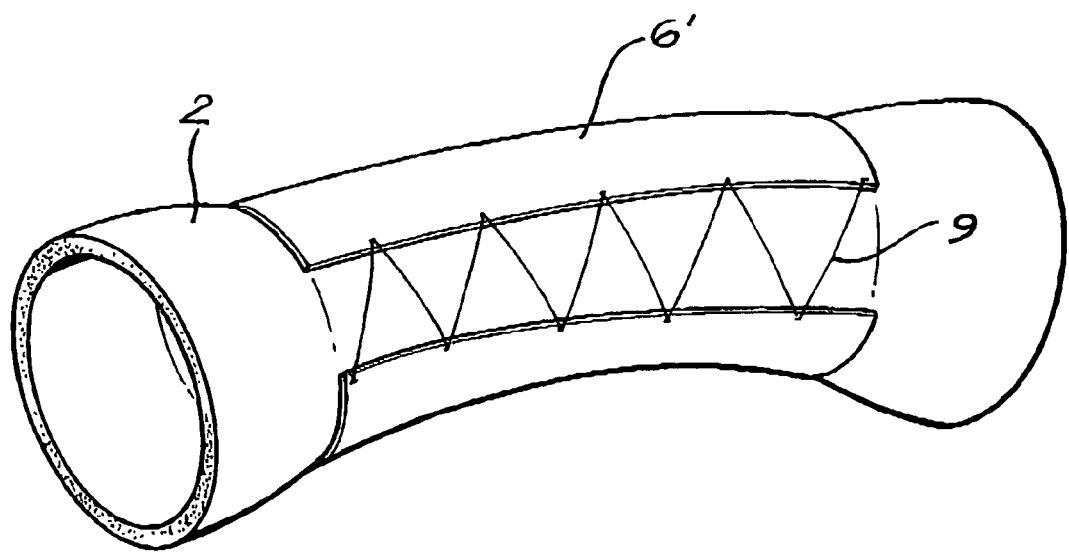
FIG. 11 is a perspective view of a portion of an aorta encased by another membrane.

Whilst the membrane sheet 6 depicted is wrapped around the entire circumferential periphery of the aorta portion 2, an effective result may still be achieved by encasing the aorta portion 2 with a membrane 6' wrapped only around a majority of the circumferential periphery of the aorta portion 2 in the manner depicted in FIG. 11. So long as the elastic membrane 6' is wrapped around more than half of the circumferential periphery of the aorta portion 2, an effective reduction of the aorta diameter will be achieved and pressure loads acting on the aorta wall will be largely taken up by the elastic membrane 6'. It is preferred that the entire circumferential periphery of the aorta portion 2 be encased by the membrane, however lack of access around the entire periphery may prevent full wrapping. Such lack of full peripheral access may particularly occur at sites where arteries branch from the aorta, such as from the descending aorta.

Figure 12:
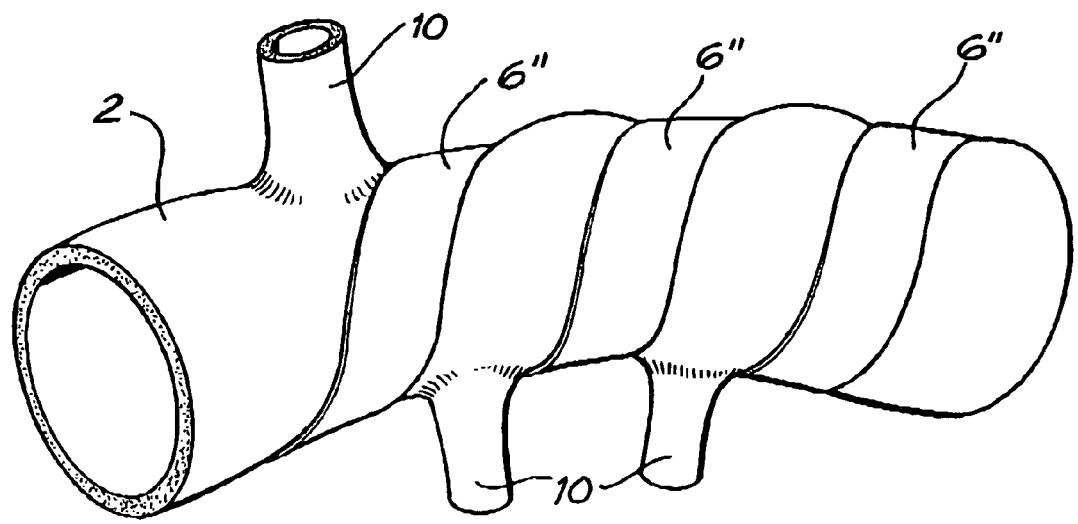
FIG. 12 is a perspective view of a portion of an aorta encased by a spiral membrane.

Referring to FIG. 12, an alternative form of elastic membrane 6" is depicted which is particularly suitable for use around a portion of the aorta 2 where multiple arteries 10 branch from the aorta 2. The elastic membrane 6" is in the form of a spiral strip of material that is spirally wound around the circumferential periphery of the aorta portion 2 to encase the same. The spacing between successive coils of the spiral can be manipulated as required to provide for passage of the arteries 10 branching from the aorta portion 2. Having the spiral membrane 6" only engage the periphery of the aorta portion 2 at discrete locations along its length will still be sufficient to reduce the diameter of the aorta portion and bear the majority of the load acting on the aorta wall to thereby increase the effective elasticity of the aorta portion 2.

Suitable classes of materials for use in fabrication of the elastic membrane 6 are elastic silicon polymers and elastic polyurethanes. Such materials are immunologically inert, durable and readily sutured, clamped or secured in various other manners. Other biocompatible elastic materials may also be utilised, such as, for example, metal/polymer composites, knitted or woven materials, or biological tissue. Use of a gel type material, such as hydrogel, encased in a membranous envelope is also envisaged. The biocompatible material may also be biological tissue.

It is also envisaged that the membrane may be formed of multiple segments of material strips having different stiffnesses for thicknesses. For example, a stiffer material may be used along either lateral side of the membrane, to reduce diameter, with a more compliant material used in the centre section of the membrane. The strips may be moulded as a one piece membrane or applied as separate adjacent membrane strips.

A particularly suitable material is an elastic silicon polymer developed by Medtronic for use as a simulated ascending aorta for in-vitro testing of artificial aortic valves. The material is typically supplied in cylindrical lengths with a wall thickness of approximately 1.25 mm and can be slit down one side to form a suitable membrane sheet 6 as depicted in FIG. 3. This material has mechanical properties similar to that of a healthy young human aorta. As the material is a silicon polymer, it has a 2-phased linear stress-strain relationship in uniaxial tensile testing, unlike the natural aorta that has a sigmoid stress-strain relation in uniaxial tensile testing. Nevertheless, the dilatation of the cylindrical material during physiologic blood flow approximates the dilatation of a healthy young aorta at normal physiologic blood flow and pressure.

The elastic membrane material is reported by the manufacturer to have a 12% compliance when pulsatile flow is pumped through the material in cylindrical form at physiological blood pressure. This 12% compliance refers to a 12% increase in diameter of the cylinder during systole at physiologic blood flow and pressure (120/70 mm Hg) as compared to the diastolic diameter of the cylinder. A stiffer elastic membrane material reported by the manufacturer as having a 4% compliance has also been used effectively, as will be described below.

Mechanical tensile testing of the elastic membrane material carried out by the present inventors has indicated that the "12% compliant" material has a tensile stress-strain curve displaying two phases, a first phase having a stiffer Young's modulus of approximately 235 kPa up to a stress of approximately 80 kPa merging into a more compliant second phase starting from approximately 120 kPa with a stiffness of approximately 62 kPa. The performance of the membrane will be dependant on the tensile stiffness multiplied by the membrane thickness. Accordingly for a 1.25 mm thick "12% compliant" membrane, the tensile stiffness×thickness is 294 N/m for the first phase and 77 N/m for the second phase. The average pressure-strain elastic modulus ($E_p$) of a cylinder formed of the "12% compliant" material, having an internal diameter of 20 mm and wall thickness of 1.25 mm at a low pulsatile pressure of 49/17 mm Hg (7/2 kPa) was measured as $0.49 \times 10^6$ dyn/cm$^2$ (49 kPa). The material was found to be too compliant at high pressures to obtain a measurement at normal physiological pressure of 120/70 mm Hg (16/9 kPa).

Mechanical tensile testing of the "4% compliant" material indicated a tensile stress-strain curve displaying two phases, a first phase having a stiffer Young's modulus of approximately 694 kPa up to a stress of approximately 240 kPa merging into a more compliant second phase starting from approximately 320 kPa with a stiffness of approximately 120 kPa. For a 1.25 mm thick "4% compliant" membrane, the tensile stiffness×thickness is 868 N/m for the first phase and 149 N/m for the second phase. The average pressure-strain elastic modulus ($E_p$) of a cylinder formed of the "4% compliant" material, having an internal diameter of 20 mm and wall thickness of 1.25 mm at a pulsatile pressure of 120/70 mm Hg (16/9 kPa) was measured as $2.2 \times 10^6$ dyn/cm$^2$ (220 kPa).

The elastic membrane sheets 6 may be fabricated and utilised in any of various lengths. If a significant length of aorta 2 is to be treated the entire effected aorta portion may be wrapped with a single elastic membrane 6 if accessibility to the aorta makes this feasible. It may be more feasible in some applications, given the confines of the treatment site, to wrap successive short lengths of elastic membrane 6 around successive portions of the aorta 2. Membrane lengths of the order of 3 cm are expected to be manageable in most applications.

For patients undergoing coronary artery bypass grafting, segments of elastic membrane may be applied to the ascending aorta and proximal arch of the aorta through the median sternotomy wound created during the bypass procedure. Segments of elastic membrane can also be applied to the distal arch and ascending thoracic aorta through a left thoracotomy or left thoracoscopic technique leaving intercostal arteries intact.

The procedure may also be undertaken on patients undergoing other forms of cardiac surgery such as valve repair or replacement, or replacement of the aortic root or ascending aorta. The procedure is also suitable for being carried out on patients undergoing thoracic surgery such as pneumonectomy, lobectomy or excision of carcinoma or any other surgical procedure where there is a risk of precipitating acute heart failure in a patient with impaired left ventricular function when aortic dilatation and stiffening are present. The procedure may also be used as a primary treatment of isolated systolic hypertension. The procedure may also be used as a primary treatment of heart failure when aortic dilatation and stiffness are present.

When the procedure is carried out during surgery where median sternotomy is not performed, the ascending aorta and arch of the aorta can be accessed through a right thoracotomy, right thoracoscopic procedure or minimal access upper hemi sternotomy.

As well as utilising the elastic membrane 6 to treat the aorta, the technique is also expected to be useful in treating similar stiffness and dilatation in the major arteries.

Whilst it is envisaged that the treatment will be suitable as a long term solution for many patients suffering cardiac failure or other problems associated with aortic stiffening, the present treatment may also be utilised as a short term solution for patients awaiting the supply of a replacement heart for heart transplant surgery. The treatment is also expected to be suitable for a short term solution to improve the cardiovascular function and strength of patients requiring coronary bypass surgery but who are perceived to be too weak to be subjected to such surgery. For such patients, a three to six month period following aortic treatment with elastic membrane wrapping may be sufficient to prepare the patient for primary bypass surgery. The treatment is also expected to be suitable for a short term solution to improve myocardial perfusion in acute coronary syndromes to improve the cardiovascular function and strength of patients requiring myocardial revascularisation (coronary artery bypass grafting, coronary angioplasty and coronary stenting). For such patients a 3 day to 1 month period following aortic treatment with an elastic wrapping may be sufficient to prepare the patient for revascularisation. Such treatments may be conducted through minimally invasive thoracoscopic techniques.

For these applications where the elastic membrane aortic treatment is conducted as a short term treatment, the elastic membrane may be formed of a biodegradable material that will degrade once its purpose has been fulfilled.

Figure 13:
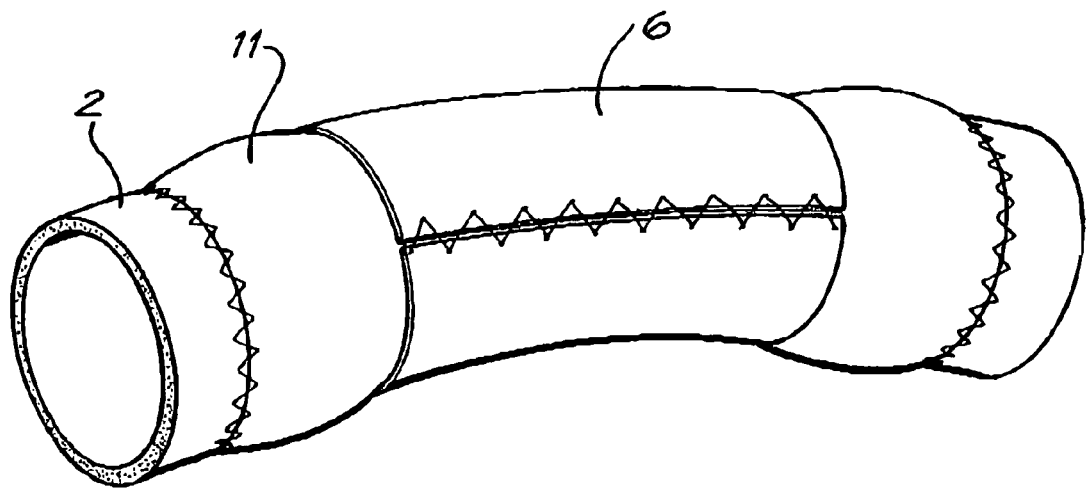
FIG. 13 is a front elevation view of an aorta having an anastomosed graft encased by an elastic membrane.

To assess the effective increase in the elasticity of the aorta by application of the elastic membrane wrap treatment described, in-vivo trials were carried out on the descending aorta of five sheep. It is to be noted that the descending aorta of a sheep is somewhat smaller than that of a human. To stimulate a dilatated and stiffened portion of aorta, a 22 mm woven polyester (Dacron) material aortic graft 11 was anastomosed in line with a resected portion of aorta 2 as depicted in FIG. 13. With the Dacron material of the graft 11 being stiff and of an increased diameter as compared to the native aorta material, the graft simulated a stiffened and dilatated aorta. The Dacron graft was then wrapped with an elastic membrane 6 as described above. Both 18 and 20 mm diameter (in unloaded state) wrapped membranes 6 were utilised, to restrict the diameter of the Dacron graft 11. Measurements of stiffness of the aorta were taken at a base line prior to to resection, following anastomosis of the Dacron graft 11, and subsequently with the elastic membrane wrap 6 in place. The stiffness measured was the average pressure-strain elastic modulus ($E_p$) over the pulsatile pressure range of physiological flow, as discussed above.

The measurements were made both at low pulse pressure (simulating normotension) and at high pulse pressure (simulating hypertension). The simulated hypertension was induced by infusion of aramine.

As expected, anastomosis of the dacron graft resulted in an increase in elastic modulus. This increase was approximately 11 times that of the base line healthy aorta in normotension and 16 times in hypertension. Addition of the elastic membrane wrap reduced the elastic modulus of the aorta by a factor of approximately 4 in normotension and 8 in hypertension to a value of approximately 2 times that of the base line healthy aorta in normotension and 3 times in hypertension.

In-vitro testing of eight human ascending aortas was also conducted, utilising a programmable gear pump to produce physiologic pulsatile pressure within the sections of ascending aorta. The ascending aorta sections were taken from cadavers ranging in age from 72 to 91 years, several of which had died of cardiac related causes. Testing of the native aortas indicated varying levels of aortic stiffening and dilatation with the average pressure-strain elastic modulus ($E_p$) at a low pulsatile pressure of 85/60 mmHg (11/8 kPa) ranging from 2.6 to $13.3 \times 10^6$ dyn/cm$^2$ (260 to 1330 kPa). At a higher pulsatile pressure of 160/90 mmHg (21/12 kPa) simulating systolic hypertension, the average pressure/strain elastic modulus was increased, varying from approximately 9.3 to $21.8 \times 10^6$ dyn/cm$^2$ (930 to 2180 kPa)

Each of the ascending aorta sections was then wrapped with "4% compliance" and "12% compliance" Medtronic membranes discussed above having a thickness of 1.25 mm. Three different diameters of membranes were utilised for each of the two membrane types, resulting in six tests for each aorta section.

The internal wrapped membrane diameters selected were based on a percentage of the mean external diameter of the ascending aorta section over a pressure range of 0 to 220 mmHg (0 to 29 kPa). The percentages selected were 91% (D1, representing a 9% diameter reduction), 82% (D2) and 70% (D3). The membrane sheets were then marked as described above to provide an indication of where the membrane end portions should be sutured to provide the required diameter of wrap in the unloaded state.

After encasing each sample, pulsatile pressures were generated within the wrapped sections of ascending aorta utilising the same pump settings that had been used to generate specific diastolic and systolic pressures in the native ascending aorta sections. Aortic diameter, systolic pressure and diastolic pressure measurements were taken.

The mean of the diastolic diameter of the aorta section specimens achieved with the various combinations of membrane material (ie 4% or 12% compliant) and unloaded membrane diameter (ie D1, D2, D3), expressed as a percentage of the native aorta diastolic diameter ($D/D_0$), is as set out in Table 1.

Figure 14:
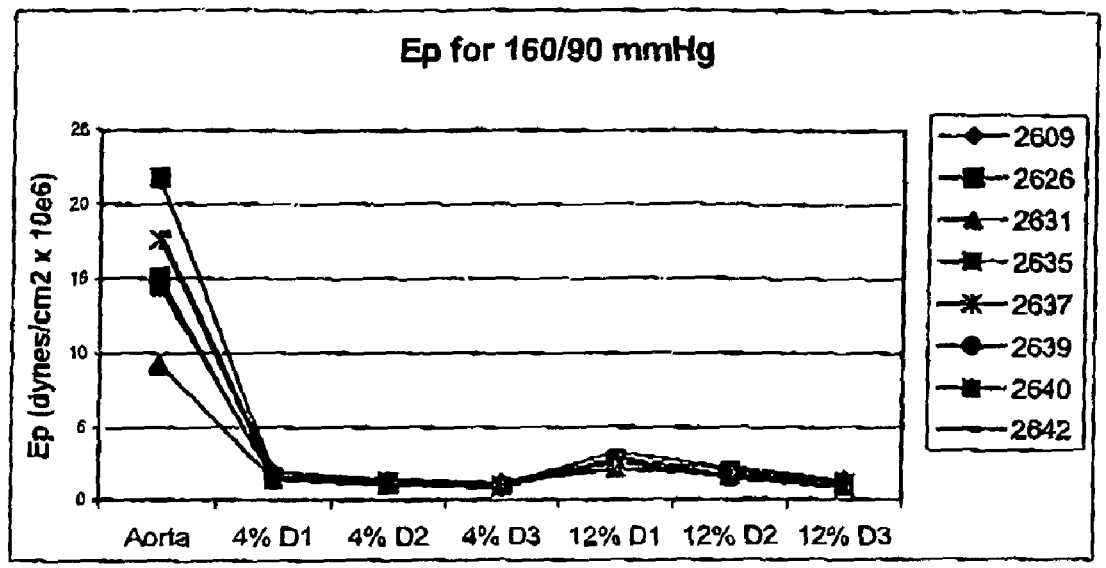
FIG. 14 is a graph depicting pressure-strain elastic modulus for sample aortas in native and encased states.

Significant reductions in the average pressure-strain elastic modulus ($E_p$) for all membrane compliance and diameter configurations were achieved across all pulsatile pressure ranges tested. The mean of the average pressure-strain elastic modulus for each of the specimens at the higher pulsatile pressure of 160/90 mmHg (21/12 kPa), for each of the various membrane configurations is set out in Table 2. The greatest reduction in pressure-strain elastic modulus, being 94%, was achieved with the "4% compliant" membrane with a 70% diameter (D3). The average pressure-strain elastic modulus results for each specimen are depicted graphically in FIG. 14.

Significant reductions in pulse pressure were also achieved, particularly for the stiffer "4% compliant" membrane and for the smaller membrane diameters. Diastolic pressures also increased, indicating a likely increase in coronary perfusion, confirming the suitability of the membrane wrapping method as suitable for the treatment of heart failure. Systolic pressure decreases were also achieved, indicating reductions in cardiac load and the suitability of the method for the treatment of isolated systolic hypertension.

Figure 15:
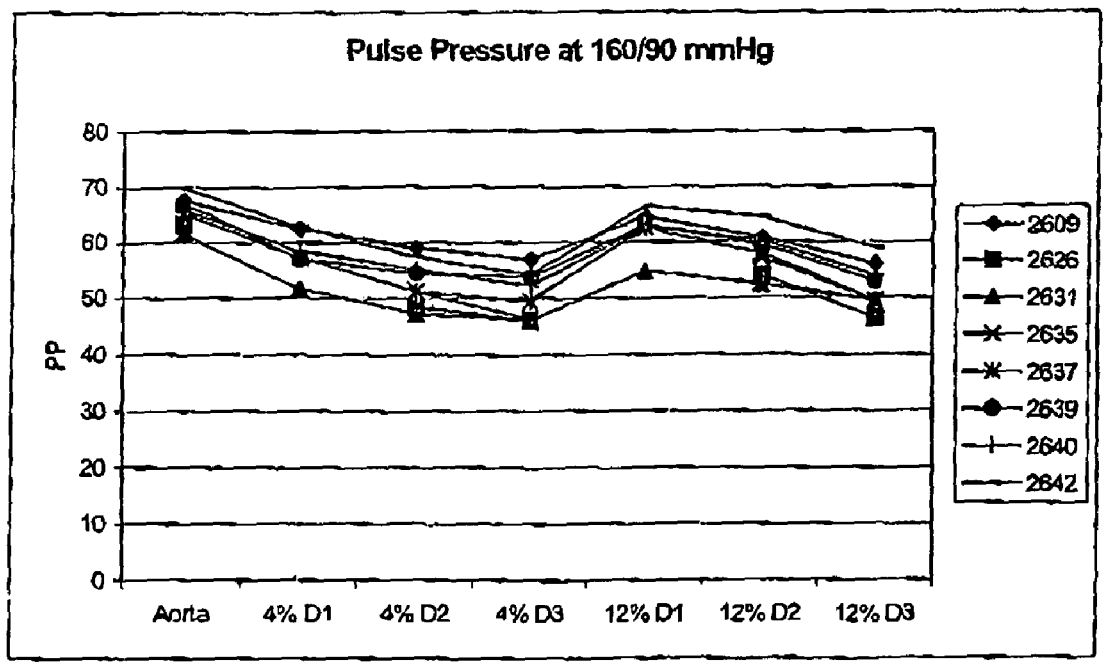
FIG. 15 is a graph depicting pulse-pressure for sample aortas in native and encased states.
Figure 16:
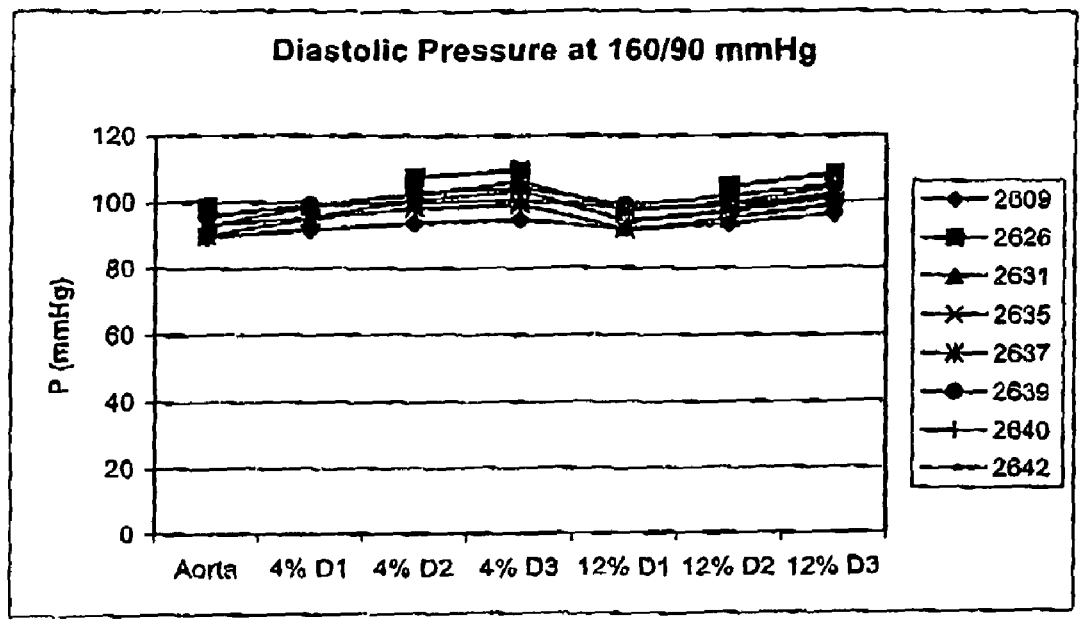
FIG. 16 is a graph depicting systolic pressure for sample aortas in native and encased states.
Figure 17:
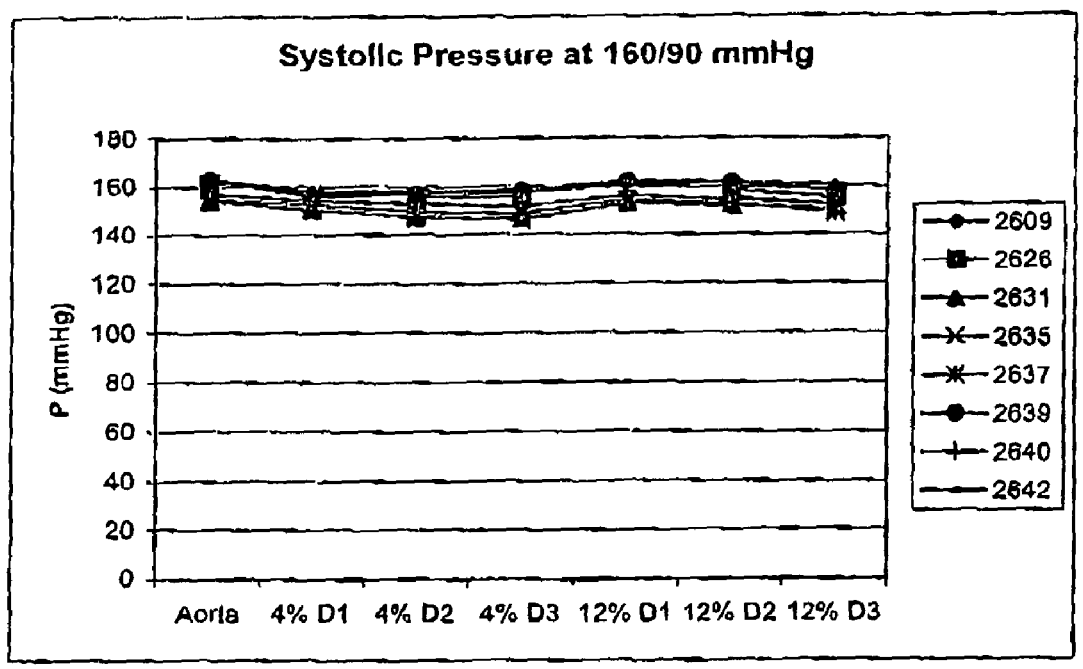
FIG. 17 is a graph depicting diastolic pressure for sample aortas in native and encased states.

The mean of the pulse pressure, diastolic pressure and systolic pressure results for each of the specimens at the higher pulsatile pressure of 160/90 mmHg (21/12 kPa), for each of the various membrane configurations, is set out in Table 3. Again, the best results were achieved with the "4% compliant" membrane and 70% diameter (D3), providing a 23% reduction in pulse pressure, 10% increase in diastolic pressure and 3.4% decrease in systolic pressure. The pulse pressure, diastolic pressure and systolic pressure results for each specimen are depicted graphically in FIGS. 15 to 17.

Figure 18:
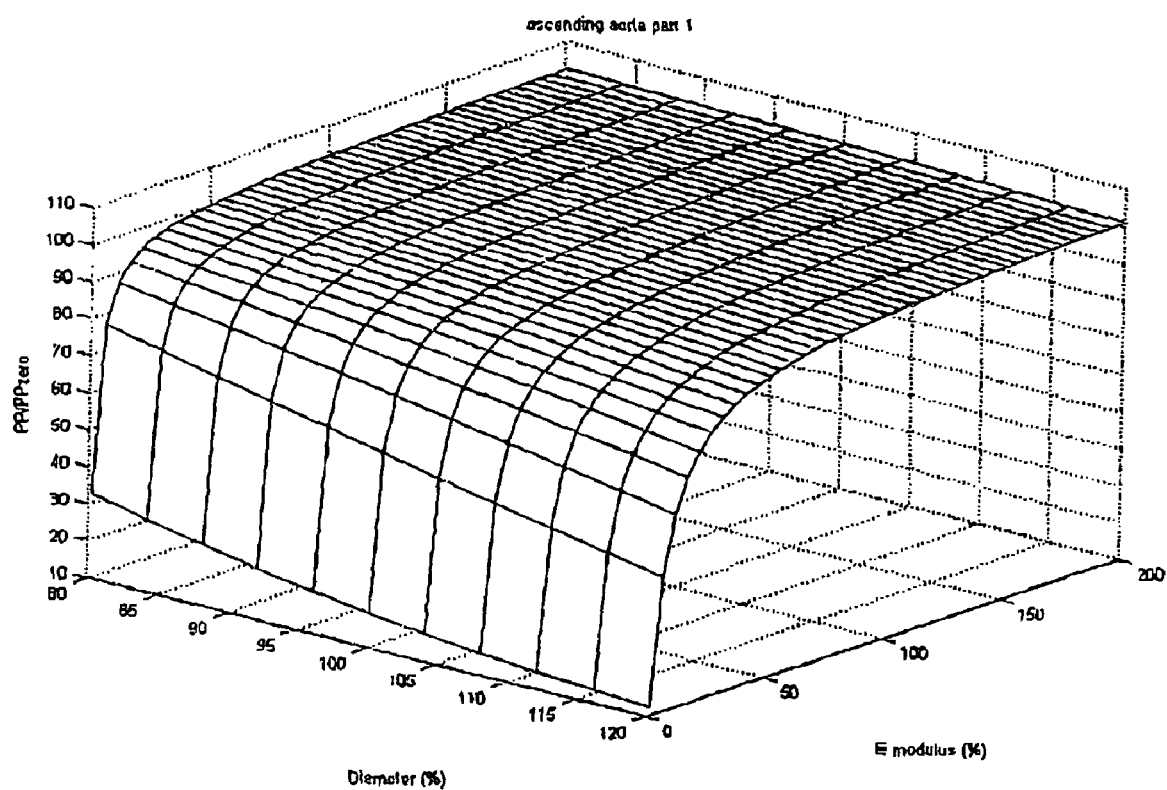
FIG. 18 is a surface plot of pulse pressure for varying aortic stiffness and diameter.
Figure 19:
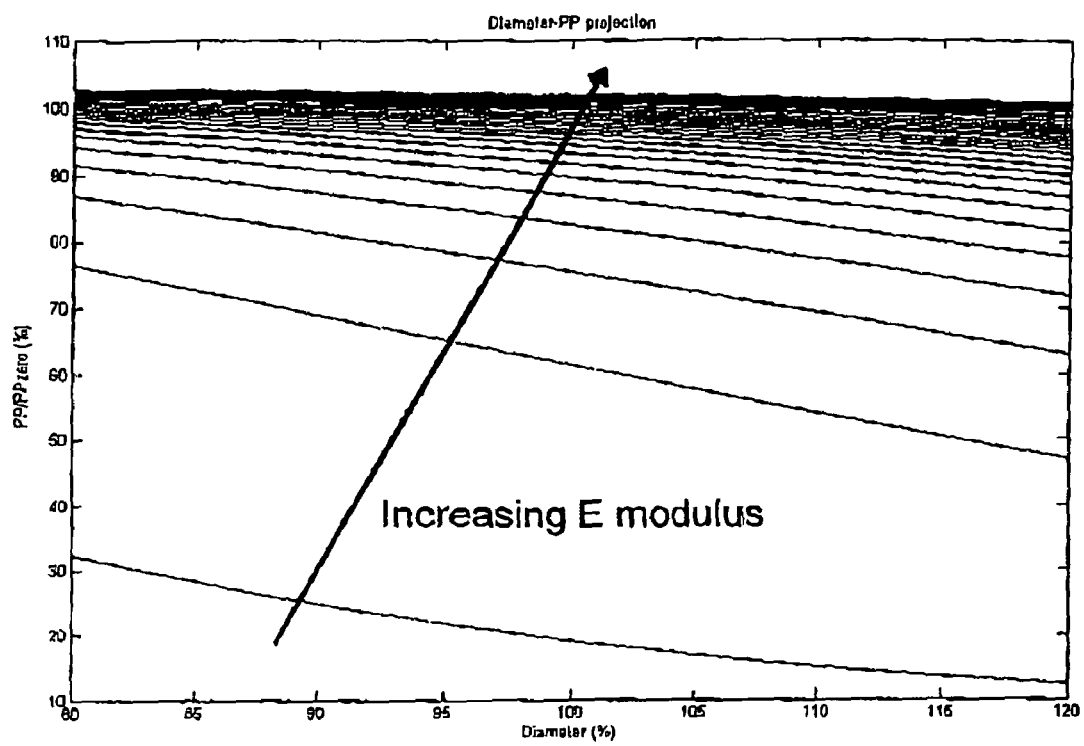
FIG. 19 is a projection of the surface plot of FIG. 18 on the diameter plane.
Figure 20:
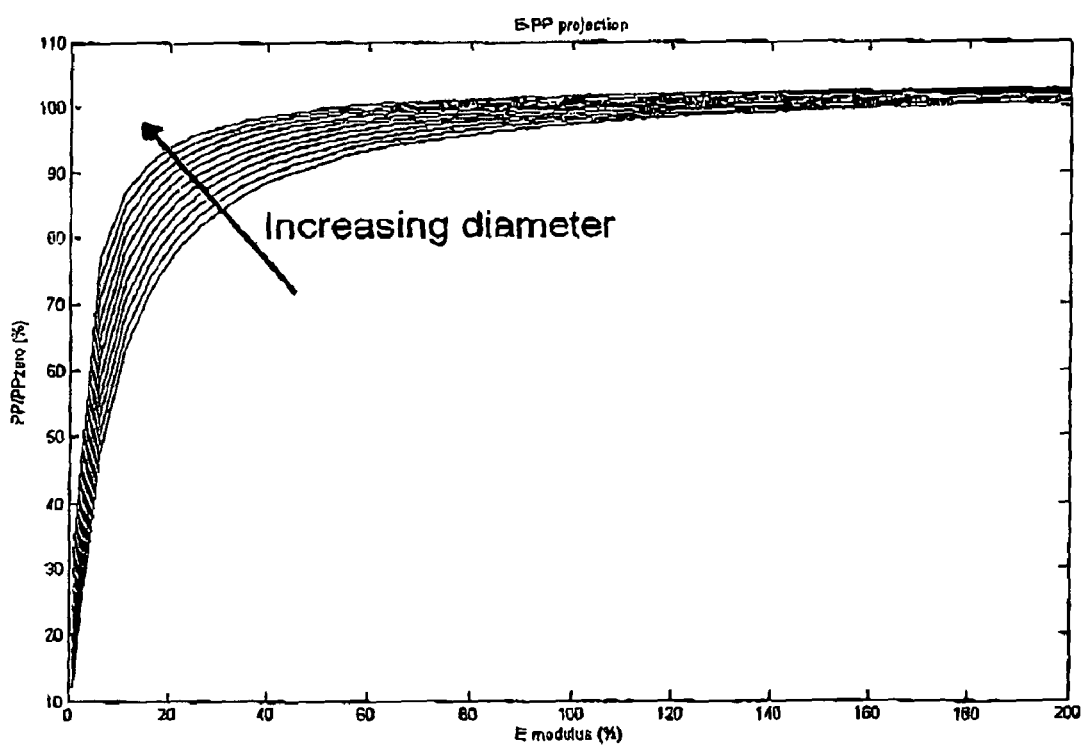
FIG. 20 is a projection of the surface plot of FIG. 18 on the stiffness plane.
Figure 21:
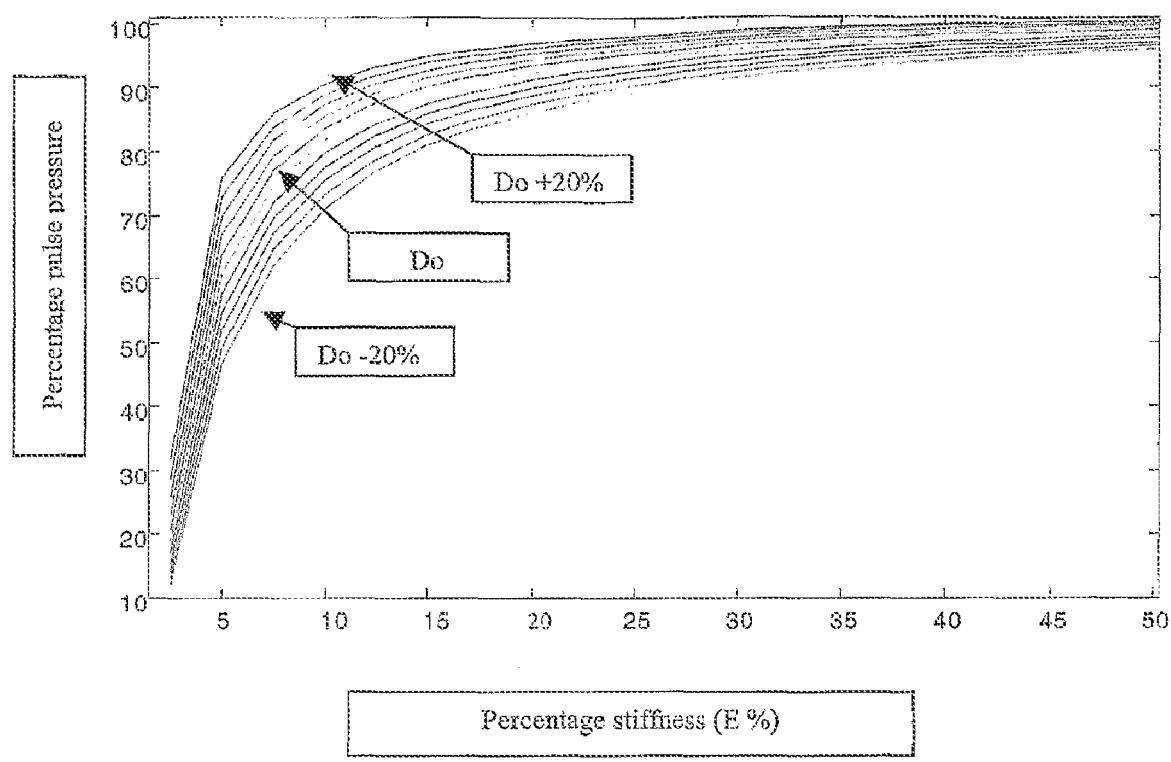
FIG. 21 is an enlarged view of a portion of the projection of FIG. 20.

A computational multi-branched arterial model has also been utilised to simulate changes in ascending aortic-stiffness and diameter. The simulation calculated the expected change in pulse pressure across an array of changes in stiffness and diameter of the ascending aorta. This model is expected to accurately simulate an ascending aorta encased in an elastic membrane as described above on the basis that the effective stiffness of the ascending aorta is determined primarily by the stiffness of the elastic membrane so long as the elastic membrane is restraining the native aorta tissue, such that the native aorta is only partially-loaded. The results were normalised for a nominal stiffness ($E_0$) and diameter ($D_0$) and are represented in Table 4, listing pulse pressure (PP) divided by the baseline pulse pressure ($PP_0$) at stiffness $E_0$ and diameter $D_0$, expressed as a percentage (%). The results are also graphically represented in FIGS. 18 to 21. FIG. 18 provides a surface plot of pulse pressure (PP) normalised against the pulse pressure ($PP_0$) at stiffness $E_0$ and diameter $D_0$. FIG. 19 provides a two dimensional projection of the data on the diameter (D) plane, whilst FIGS. 20 and 21 provide projections of the data onto the stiffness plane (E).

A comparison of specific results obtained with the human in-vitro testing have provided a satisfactory correlation with the computational estimations, such that the computational model can confidently be used to investigate the effects of a given membrane stiffness and wrapped diameter to achieve a desired reduction in pulse pressure, and hence dynamic load on the left ventricle of the heart.

As indicated by the computational results, a reduction in vessel diameter (D), whilst maintaining a constant stiffness (E), will actually result in an increase in pulse pressure (PP), as a result of the constriction in the vessel flow path through which the blood is able to flow. A decrease in stiffness (E), whilst maintaining a constant diameter (D), results in a decrease in pulse pressure (PP).

Whilst a reduction in diameter per se provides an increase in pulse pressure, perhaps suggesting that a reduction in diameter is to be avoided, a reduction in the diameter is necessary when applying the elastic membrane so as to reduce the effective stiffness of the blood vessel being wrapped, from that of the native tissue to approximately that of the elastic membrane. If significant reductions in stiffness can be achieved, then it can be seen that the reduction in pulse pressure resulting from the reduced stiffness will be much more significant than the increase in pulse pressure resulting from the decreased diameter. There is thus a balance between providing a diameter reduction that is sufficient for an elastic membrane of a given reduced stiffness to take most of the pressure load for pressures from diastolic pressure up to systolic pressure, whilst not being so substantial that it adversely constricts blood flow.

The ideal combination of elastic membrane stiffness and blood vessel diameter reduction will vary dependent upon the specific application, although the stiffness of the native blood vessel will not appreciably effect this selection.

Based on the in-vitro and computational results, reductions in diastolic diameter of a blood vessel of between 10% and 50% are expected to be particularly suitable. For the ascending aorta, reductions in diastolic external diameter to between 18 mm and 30 mm at a normal diastolic pressure of 70 mmHg (9 kPa) are expected to be particularly suitable without adversely constricting the blood flow passage. For young humans, reductions in diastolic external diameter of the ascending aorta down to 10 mm may be suitable.

A measurement of elastic membrane tensile stiffness× thickness of between 25 and 2500 N/m is also expected to be suitable when treating the aorta, particularly the ascending aorta, with measurements between 50 and 1000 N/m being particularly suitable.

Considering the average pressure-strain elastic modulus of the membrane itself, a modulus of between $0.15 \times 10^6$ and $15 \times 10^6$ dyn/cm$^2$ for a cylinder formed of the membrane with an internal diameter of 20 mm at a pulsatile pressure of 120/70 mmHg (16/9 kPa) is expected to be suitable, with a modulus of between $0.3 \times 10^6$ and $6 \times 10^6$ dyn/cm$^2$ being particularly suitable.

The computational modelling has also established that the procedure of encasing a blood vessel with an elastic membrane is most effective when applied to the ascending aorta. Whilst improvements are achieved by encasing other stiffened blood vessels, particularly other portions of the aorta, the reductions in pulse pressure are much less than those that can be achieved by encasing the ascending aorta. The ascending aorta is also free of intercostal artery branches, and hence it is also a very suitable blood vessel for encasing in terms of surgical simplicity, as a single sheet membrane can be readily applied to the ascending aorta. The modelling further indicated that there is little additional benefit achieved by encasing other portions of the aorta rather than just the ascending aorta and proximal arch of the aorta.

As well as treating native blood vessels that have been stiffened by any of various mechanisms, whether associated with dilatation or not, the method described is also applicable to treating blood vessels that have been stiffened by grafting a synthetic blood vessel portion in line with the native tissue. Such grafts, typically formed from non-compliant woven polyester material, such as Dacron, are often utilised to replace sections of the aorta which have been damaged, particularly to remove aneurysms. Other grafts, such as polytetrafluoroethylene (PTFE) or Gore-Tex® grafts may similarly be treated. As can be seen from the sheep in-vivo testing results above, the application of a non-compliant graft results in significant effective stiffening of a blood vessel, which can be suitably treated by the application of an elastic membrane wrap to the graft in the manner described.

The above described method may be applied as a stand alone procedure, or may be applied in conjunction with drug or agent (pharmacological, cellular, gene or otherwise) therapies. It is also envisaged that such drugs or agents might be incorporated within, or applied to, the elastic membrane prior to encasing the blood vessel being treated, thereby providing direct delivery of the drug or agent. The method is also applicable to both human and animal subjects. The method described is both simple to apply, and has a reduced possibility of complication compared to various other known treatments, given that the membrane device is non-blood contacting, being applied to the exterior of the blood vessel, and is a passive device.

TABLE 1

Mean Aortic Diameter for Various Membrane Configurations

| Membrane | D (mm) | D/D$_0$ |
|---|---|---|
| Native Aorta | 32.2 (D$_0$) | 100% |
| 4% D1 | 26.1 | 80.6% |
| 4% D2 | 25.3 | 78.5% |
| 4% D3 | 22.5 | 69.7% |
| 12% D1 | 27.8 | 86.3% |
| 12% D2 | 27.8 | 86.1% |
| 12% D3 | 25.8 | 80.1% |

Mean Average Pressure-Strain Elastic Modulus for Various Membrane Configurations

| Membrane | E$_p$dyn/cm$^2 \times 10^6$ | E$_p$/E$_{p0}$ |
|---|---|---|
| Native aorta | 15.93 (E$_{p0}$) | 100% |
| 4% D1 | 1.75 | 11.0% |
| 4% D2 | 1.21 | 7.6% |
| 4% D3 | 0.97 | 6.1% |
| 12% D1 | 2.78 | 17.4% |
| 12% D2 | 1.84 | 11.6% |
| 12% D3 | 1.07 | 6.7% |

TABLE 3

Mean Pulse, Diastolic and Systolic Pressures for Various Membrane Configurations

| Memb. | Pulse Pressure (PP) mmHg | PP/PP$_0$ | Diastolic Pressure (DP) mmHg | DP/DP$_0$ | Systolic Pressure (SP) mmHg | SP/SP$_0$ |
|---|---|---|---|---|---|---|
| Native aorta | 65.8 (PP$_0$) | 100% | 93.7 (DP$_0$) | 100% | 159.5 (SP$_0$) | 100% |
| 4% D1 | 58.2 | 88.5% | 96.9 | 103.4% | 155.1 | 97.3% |
| 4% D2 | 53.1 | 80.7% | 101.4 | 108.2% | 154.4 | 96.8% |
| 4% D3 | 50.7 | 77.0% | 103.0 | 110.0% | 153.7 | 96.4% |
| 12% D1 | 62.6 | 95.2% | 95.1 | 101.5% | 157.8 | 98.9% |
| 12% D2 | 58.3 | 88.7% | 98.3 | 104.9% | 156.7 | 98.2% |
| 12% D3 | 52.1 | 79.1% | 102.2 | 109.0% | 154.3 | 96.7% |

TABLE 4

Estimated PP/PP$_0$ (%) for Varying Radius and Elastic Modulus

| E/E$_0$ (%) | 0.80D$_0$ | 0.84D$_0$ | 0.88D$_0$ | 0.92D$_0$ | 0.96D$_0$ | D$_0$ | 1.04D$_0$ | 1.08D$_0$ | 1.12D$_0$ | 1.16D$_0$ | 1.20D$_0$ |
|---|---|---|---|---|---|---|---|---|---|---|---|
| 1 | 32.4 | 29.1 | 26.2 | 23.5 | 21.2 | 19.1 | 17.3 | 15.7 | 14.4 | 13.3 | 12.4 |
| 6 | 76.6 | 73.6 | 70.5 | 67.4 | 64.4 | 61.3 | 58.3 | 55.3 | 52.5 | 49.7 | 47.0 |
| 11 | 86.9 | 84.8 | 82.6 | 80.3 | 78.0 | 75.5 | 73.0 | 70.5 | 68.0 | 65.4 | 62.9 |
| 16 | 91.6 | 90.0 | 88.3 | 86.5 | 84.6 | 82.6 | 80.6 | 78.5 | 76.3 | 74.1 | 71.9 |
| 21 | 94.2 | 92.9 | 91.6 | 90.1 | 8S.6 | 86.9 | 85.2 | 83.4 | 81.5 | 79.6 | 77.7 |
| 26 | 95.9 | 94.9 | 93.7 | 92.5 | 91.2 | 89.8 | 88.3 | 86.7 | 85.1 | 83.4 | 81.7 |
| 31 | 97.1 | 96.2 | 95.2 | 94.2 | 93.0 | 93.3 | 90.5 | 89.2 | 87.7 | 86.2 | 84.7 |
| 36 | 98.0 | 97.2 | 96.4 | 95.4 | 94.4 | 91.8 | 92.2 | 91.0 | 89.7 | 88.4 | 87.0 |
| 41 | 98.6 | 98.0 | 97.2 | 96.4 | 95.5 | 94.5 | 93.5 | 92.4 | 91.3 | 90.0 | 88.8 |
| 46 | 99.2 | 98.6 | 97.9 | 97.2 | 96.4 | 95.5 | 94.6 | 93.6 | 92.5 | 91.4 | 90.2 |
| 51 | 99.6 | 99.1 | 98.5 | 97.8 | 97.1 | 96.3 | 95.4 | 94.5 | 93.5 | 92.5 | 91.4 |
| 55 | 100.0 | 99.5 | 98.9 | 98.3 | 97.7 | 96.9 | 96.1 | 95.3 | 94.4 | 93.5 | 92.5 |
| 60 | 100.3 | 99.8 | 99.3 | 98.8 | 98.1 | 97.5 | 96.7 | 96.0 | 95.1 | 94.3 | 93.3 |
| 65 | 100.5 | 100.1 | 99.7 | 99.1 | 98.6 | 97.9 | 97.3 | 96.5 | 95.8 | 94.9 | 94.1 |
| 70 | 100.7 | 100.4 | 99.9 | 99.5 | 98.9 | 98.4 | 97.7 | 97.0 | 96.3 | 95.5 | 94.7 |
| 75 | 100.9 | 100.6 | 100.2 | 99.8 | 99.3 | 98.7 | 98.1 | 97.5 | 96.8 | 96.1 | 95.3 |
| 80 | 101.1 | 100.8 | 100.4 | 100.0 | 99.5 | 99.0 | 98.5 | 97.9 | 97.2 | 96.5 | 95.8 |
| 85 | 101.2 | 101.0 | 100.6 | 100.2 | 99.8 | 99.3 | 98.8 | 98.2 | 97.6 | 97.0 | 96.3 |
| 90 | 101.4 | 101.1 | 100.8 | 100.4 | 100.0 | 99.6 | 99.1 | 98.5 | 98.0 | 97.3 | 96.7 |
| 95 | 101.5 | 101.3 | 101.0 | 100.6 | 100.2 | 99.8 | 99.3 | 98.8 | 98.3 | 97.7 | 97.0 |
| 100 | 101.6 | 101.4 | 101.1 | 100.8 | 100.4 | 100.0 | 99.6 | 99.1 | 98.5 | 98.0 | 97.4 |
| 105 | 101.7 | 101.5 | 101.2 | 100.9 | 100.6 | 100.2 | 99.8 | 99.3 | 98.8 | 98.3 | 97.7 |
| 110 | 101.8 | 101.6 | 101.3 | 101.1 | 100.7 | 100.4 | 100.0 | 99.5 | 99.0 | 98.5 | 98.0 |
| 115 | 101.9 | 101.7 | 101.5 | 101.2 | 100.9 | 100.5 | 100.1 | 99.7 | 99.2 | 98.7 | 98.2 |
| 120 | 102.0 | 101.8 | 101.6 | 101.3 | 101.0 | 100.7 | 100.3 | 99.9 | 99.4 | 99.0 | 98.5 |

The invention claimed is:

1. A method of treating a stiffened blood vessel, said method comprising at least substantially encasing a stiffened portion of said blood vessel with an elastic membrane formed of biocompatible material, such that said membrane engages said stiffened portion of said blood vessel to thereby reduce the external diameter of said stiffened portion of said blood vessel, passively carry at least a portion of blood pressure loads acting on said blood vessel throughout systole and diastole and reduce the effective stiffness of said stiffened portion of said blood vessel, said elastic membrane having a stiffness less than the stiffness of said stiffened portion of said blood vessel.

2. The method of claim 1 wherein said blood vessel is an artery.

3. The method of claim 2 wherein said blood vessel is the aorta.

4. The method of claim 2 wherein said blood vessel is the ascending aorta.

5. The method of claim 4 wherein said external diameter of said stiffened portion of said blood vessel is reduced to between 18 mm and 30 mm at a pressure of 70 mmHg (9 kPa).

6. The method of claim 1 wherein said stiffened portion of said blood vessel is a grafted synthetic portion of said blood vessel.

7. The method of claim 6 wherein said grafted synthetic portion is a woven polyester graft.

8. The method of claim 1 wherein said stiffened portion of said blood vessel is in a stiffened and dilatated state prior to treatment.

9. The method of claim 1 wherein said membrane is in the form of a sheet, said stiffened portion of said blood vessel being encased by wrapping said membrane sheet around the circumferential periphery of said stiffened portion of said blood vessel and securing opposing end portions of said membrane.

10. The method of claim 9 wherein said membrane sheet is wrapped around the entire circumferential periphery of said stiffened portion of said blood vessel portion.

11. The method of claim 9 wherein said membrane sheet is wrapped about a majority of the circumferential periphery of said stiffened portion of said blood vessel.

12. The method of claim 9 wherein the opposing end portions of said membrane sheet are secured by suturing.

13. The method of claim 9 wherein the opposing end portions of said membrane are secured by way of a clamp.

14. The method of claim 9 wherein the opposing end portions of said membrane are secured by welding.

15. The method of claim 9 wherein the opposing end portions of said membrane are secured by way of interlocking structures formed on, or fixed to, each of said opposing end portions.

16. The method of claim 9 wherein each opposing end portion is provided with a marking extending generally parallel with a free end edge of said end portion, said end portions being secured along or adjacent to said markings.

17. The method of claim 9 wherein said membrane sheet is formed by slitting a cylindrical membrane.

18. The method of claim 9, wherein said membrane, when formed into a cylinder having an internal diameter of 20 mm, has an average pressure-strain elastic modulus of between $0.15 \times 10^6$ and $15 \times 10^6$ dyn/cm$^2$ at a pulsatile pressure of 120/70 mmHg (16/9 kPa).

19. The method of claim 9, wherein said membrane, when formed into a cylinder having an internal diameter of 20 mm, has an average pressure-strain elastic modulus of between $0.3 \times 10^6$ and $6 \times 10^6$ dyn/cm$^2$ at a pulsatile pressure of 120/70 mmHg (16/9 kPa).

20. The method of claim 1 wherein said membrane is in the form of a spiral, said stiffened portion of said blood vessel being encased by spirally wrapping said membrane spiral around the circumferential periphery of said stiffened portion of said blood vessel.

21. The method of claim 1 wherein said membrane has a stiffness approximating that of a non-stiffened blood vessel of the type of blood vessel being treated.

22. The method of claim 1 wherein said membrane has a measurement of tensile stiffness×thickness of between 25 and 2500 N/m.

23. The method of claim 22 wherein said measurement of tensile stiffness×thickness is between 50 and 1000 N/m.

24. The method of claim 1 wherein said external diameter of said stiffened portion of said blood vessel is reduced by between 10% and 50% when encased with said membrane, at a pressure of 70 mmHg (9 kPa).

25. The method of claim 1 wherein said membrane is formed of an elastic silicon polymer.

26. The membrane of claim 1 wherein said membrane is formed of an elastic polyurethane.

27. The method of claim 1 wherein said method is carried out thoracoscopically.

28. A method of treating a blood vessel, said blood vessel having a native tissue portion and a synthetic portion grafted in line with said native tissue portion, said synthetic portion having a greater stiffness than the stiffness of said native tissue portion, said method comprising at least substantially encasing said synthetic portion with an elastic membrane formed of biocompatible material such that said membrane engages said synthetic portion to thereby reduce the external diameter of said synthetic portion, passively carry at least a portion of blood pressure loads acting on said blood vessel throughout systole and diastole and reduce the effective stiffness of said synthetic portion of said blood vessel, said elastic membrane having a stiffness less than the stiffness of said synthetic portion of said blood vessel.

29. The method of claim 28 wherein said synthetic portion is a woven polyester.

* * * * *